United States Patent

Harada et al.

[11] Patent Number: 6,159,283
[45] Date of Patent: Dec. 12, 2000

[54] APPARATUS AND METHOD FOR MEASURING MECHANICAL STRENGTH OF NECK PORTION OF SEED CRYSTAL AND METHOD FOR PRODUCING SILICON SINGLE CRYSTAL

[75] Inventors: Isamu Harada; Michiaki Oda; Masaru Toyoshima; Toshinari Murai; Eiichi Iino, all of Gunma-ken, Japan

[73] Assignee: Shin-Etsu Handotai Co., Ltd., Tokyo, Japan

[21] Appl. No.: 09/267,214

[22] Filed: Mar. 12, 1999

[30] Foreign Application Priority Data

Mar. 13, 1998 [JP] Japan .................................. 10-082608

[51] Int. Cl.[7] .................................................... C30B 15/24

[52] U.S. Cl. ............................. 117/13; 117/217; 117/911

[58] Field of Search ............................... 117/13, 14, 217, 117/218, 911

[56] References Cited

U.S. PATENT DOCUMENTS 5,932,007 9/1999 Li ............................................. 117/208
5,948,164 9/1999 Iida et al. ................................. 117/218

*Primary Examiner*—Felisa Hiteshew
*Attorney, Agent, or Firm*—Hogan & Hartson, LLP

[57] ABSTRACT

Apparatus for measuring the mechanical strength of a neck portion of a silicon seed crystal used for growing a silicon crystal by the Czochralski method includes a seed chuck for holding the seed crystal of a test sample and an end of a wire hung from an upper hook. A crystal holder which holds the other end part of the test sample from below is tied to a lower hook with another wire to support the holder. The apparatus includes means for pulling the hook at a given rate, and measuring means for continuously measuring tensile load. Such apparatus and the method thereby provide accurate measurement of mechanical strength of the neck portion of the silicon seed crystal with good precision and reproducibility. A single crystal ingot is grown under conditions affording good balance of productivity and safety.

5 Claims, 4 Drawing Sheets

CROSS SECTION AT 2B-2B

RESULT OF TENSILE STRENGTH TEST

APPARATUS AND METHOD FOR MEASURING MECHANICAL STRENGTH OF NECK PORTION OF SEED CRYSTAL AND METHOD FOR PRODUCING SILICON SINGLE CRYSTAL

BACKGROUND OF THE INVENTION

1. Field of the Invention

The present invention relates to an apparatus and method for measuring mechanical strength of neck portion of a seed crystal used for growing a silicon single crystal ingot according to the Czochralski method (CZ method), and a method for producing a silicon single crystal.

2. Description of the Related Art:

In the conventional methods of producing a silicon single crystal according to the CZ method, a silicon single crystal is used as a seed crystal, which is brought into contact with silicon melt and then slowly pulled while being rotated to grow a silicon single crystal ingot. In such methods, after the seed crystal is brought into contact with a silicon melt, the so-called necking is performed to form a neck portion having a smaller diameter of around 3 mm. Subsequently, the diameter of the crystal is increased to a predetermined size, and then a dislocation-free silicon single crystal is pulled upwardly.

In this case, the formation of the neck portion enables a single crystal to grow while eliminating dislocation propagated to the straight body following the seed crystal from slip dislocation generated in the seed crystal in high density due to thermal shock which occurs when the seed crystal is brought into contact with silicon melt. However, the crystal weight has recently been getting heavier with use of a larger diameter of single crystals and with the purpose of improving productivity, and therefore mechanical strength of the seed crystal and the neck portion are likely to be insufficient. On the other hand, length of the neck portion itself is getting longer because of automatization of the necking operation and use of larger seed crystals for holding heavier crystals. If the single crystal ingot falls due to breakage of recessed portion of the seed crystal for pin fixation thereof in a seed holder, the neck portion having a small diameter or the like, it may lead to a serious accident.

Therefore, the tensile fracture strength of silicon single crystals becomes important. However, the values of tensile fracture strength of the neck portion determined by a conventional universal tensile tester used for tensile test of metals or the like significantly fluctuate even if the values are sorted out according to the diameters of test pieces corresponding to the thickness of the neck portion, and thus a true value of tensile fracture strength can hardly be obtained. In addition, even if the universal tensile tester is provided with a heater in order to obtain a value under high temperature environment as in an actual single crystal pulling apparatus, highly reliable data cannot necessarily be obtained.

Moreover, because of the characteristic of the crystal, the neck portion is easily destroyed when shearing force (force acting on the transverse direction) is applied, and thus accurate data cannot be obtained.

In particular, under the current circumstance where a longer neck portion as long as 20 cm is used because of the use of larger seed crystal and automatization of the necking operation, the measurement error due to the shearing force has become larger and a problem in obtaining the true value.

Therefore, emphasis on safety as to probability of accidental breakage of a seed crystal or neck portion, which is expected to increase with the growth of larger diameter and larger weight of silicon single crystal, may lead to an excessively high safety factor, and it has reduced the productivity and increased the cost.

SUMMARY OF THE INVENTION

The present invention has been completed to solve the aforementioned problems of the prior art. Thus, the major object of the present invention is to develop an apparatus for accurately measuring mechanical strength of neck portion of a silicon seed crystal with good precision and reproducibility, establish a method for measuring the same, and provide a method for producing a silicon single crystal wherein a single crystal ingot is grown under operating conditions affording good balance of productivity and safety, which conditions have been found based on the data obtained by the aforementioned apparatus and method.

To achieve the aforementioned object, the present invention provides an apparatus for measuring mechanical strength of a neck portion of silicon seed crystal used for growing a silicon single crystal by the Czochralski method, wherein the apparatus has a structure that a seed chuck for holding a seed crystal of a test sample is provided at an end of a wire hung from an upper hook, and a crystal holder for holding the other end part of the test sample from below is tied to a lower hook with another wire to support the holder, and comprises a means for pulling the hook(s) at a predetermined rate, and a means for continuously measuring tensile load.

In this way, by connecting the upper hook and the upper seed chuck, and the lower crystal holder and the lower hook with a wire respectively, the upper seed chuck and the lower crystal holder holding the test sample can be accurately positioned along the vertical axis between the upper hook and the lower hook. Thus, force is applied to the test sample only in the vertical direction, and hence a true value of tensile fracture strength of the neck portion of the seed crystal can be obtained. Further, if a safety factor calculated from tensile fracture strength obtained based on measurement by the aforementioned apparatus is used as a condition for the production of single crystal, it will sufficiently meet security against the future production of further larger diameter and heavier weight of silicon single crystal.

In the aforementioned apparatus, the crystal holder preferably comprises a reversed bowl-like member for holding a conical section of a small diameter corn-shaped portion of the test sample following the neck portion thereof, and a bowl-like member engaged with the reversed bowl-like member.

The test sample to be measured in the measuring apparatus of the present invention having the aforementioned structure is a sample taken from actually operating apparatus for pulling single crystals, not a so-called test piece which is cut out from an ordinary material, and the internal surface of the crystal holder is formed to meet the shape of the sample. Therefore, the crystal holder can accommodate the small diameter corn-shaped portion and rounded tail without undue force applied to the crystal holder, and hence uniform load is applied to the small diameter corn-shaped portion during the pulling, thereby affording an accurate tensile fracture strength value.

The aforementioned apparatus can further comprise a heating mechanism to permit measurement of mechanical strength of neck portion under high temperature environment.

In such an apparatus, the test sample can be placed in the same temperature condition as an actually operating apparatus for pulling single crystals, and thus it becomes possible to measure more accurate and precise tensile fracture strength.

According to another aspect of the present invention, there is provided a method for measuring mechanical strength of a neck portion of silicon seed crystal used for growing a silicon single crystal by the Czochralski method, wherein a seed crystal of a test sample which comprises the seed crystal/neck portion/corn-shaped portion/rounded tail and is produced by an apparatus for pulling a silicon single crystal, is inserted into a seed chuck provided at an end of a wire hung from an upper hook and held thereby, the small diameter corn-shaped portion/rounded tail of the sample is fixed in a crystal holder which is tied to a lower hook with another wire, and then the hook(s) is(are) pulled at a predetermined rate to measure tensile fracture strength.

In the aforementioned method, the seed crystal holding mechanism and the pulling mechanism using wires of the measuring apparatus are applied with tensile load under approximately the same condition as that in a practical apparatus for pulling single crystals, and the test sample is one taken from actually operating pulling apparatus, and has a shape comprising seed crystal, neck portion, small diameter corn-shaped portion and rounded tail. Therefore, the test sample can be set between the seed chuck and the crystal holder without being applied with undue force. As for the pulling operation, because the pulling can be surely performed along the perpendicular axis between the upper hook and the lower hook, a true value of tensile fracture strength can be obtained. In addition, it is also possible to evaluate breakage including those of actually used wires and seed crystal holding device under a high temperature condition similar to that of the practical use. Thus, the measuring method affords higher safety when considering the pulling process as a whole.

According to a further aspect of the present invention, there is provided a method for producing a silicon single crystal wherein pulling operation in growing a silicon single crystal by the Czochralski method is performed so that load applied to a neck portion of silicon seed crystal should be 15.85 kgf/mm$^2$ or less.

As clearly seen from FIG. 4, by performing the pulling operation so that load applied to a neck portion of silicon seed crystal as an actually measured value should be 15.85 kgf/mm$^2$ or less as defined above, possibility of breakage at least at the seed crystal or the neck portion is eliminated of course at ordinary temperature and even at a high Temperature of 700° C. or more within the range of 6 mm or less of the neck portion diameter.

In the aforementioned method, the pulling operation is preferably performed so that the load applied to a neck portion of silicon single crystal should be 0.9×15.85 kgf/mm$^2$ or less considering a safety factor.

Thus, because the measuring apparatuses and the measuring methods of the present invention enable measurement of true mechanical strength, if a safety factor calculated from tensile fracture strength obtained based on measurement by the aforementioned apparatus and method is used as a condition for the production of single crystal, it will sufficiently meet security against future production of larger diameter and larger weight of silicon single crystal.

In the aforementioned method, the pulling operation is preferably performed so that the load applied to a neck portion of a silicon single crystal should be 0.6×15.85 kgf/mm$^2$ or more.

By providing a lower limit as defined above, productivity above a certain level can be ensured. Formerly, because the mechanical strength of the wire was indefinite and hence the upwardly pulling weight was unduly reduced, and unduly high safety factor was used, thereby the productivity and the production yield were deteriorated. In contrast, according to the present invention, a predetermined productivity can be achieved by establishing the lower limit. In addition, by defining the lower limit as 60% or more of the critical value, the lifetime of the wires can be prolonged.

Because an accurate value of the mechanical strength of neck portion can be obtained according to the present invention, by using a safety factor calculated from the value for the condition of the production of single crystals, it will be possible to sufficiently meet the requirement for security against future production of larger diameter and larger weight of silicon single crystal, and markedly improve productivity, production yield, and cost.

DESCRIPTION OF THE INVENTION AND EMBODIMENTS

The present invention and embodiments thereof will be explained hereinafter with reference to the appended drawings, but the scope of the present invention is not limited to them.

The inventors of the present invention considered it is accidental breakage of the seed crystal or the neck portion that will be an obstacle to the future tendency to a further larger diameter and weight, and it is essential to know accurate tensile fracture strength of the seed crystal or the neck portion in order to prevent the breakage, and studied the cause of failing in obtaining accurate data by conventional measuring apparatuses. As a result, the inventors found that there is a problem particularly in the method for holding the test sample, successfully improved it and established various conditions therefor. Thus, the present invention has been completed.

Figure 1:
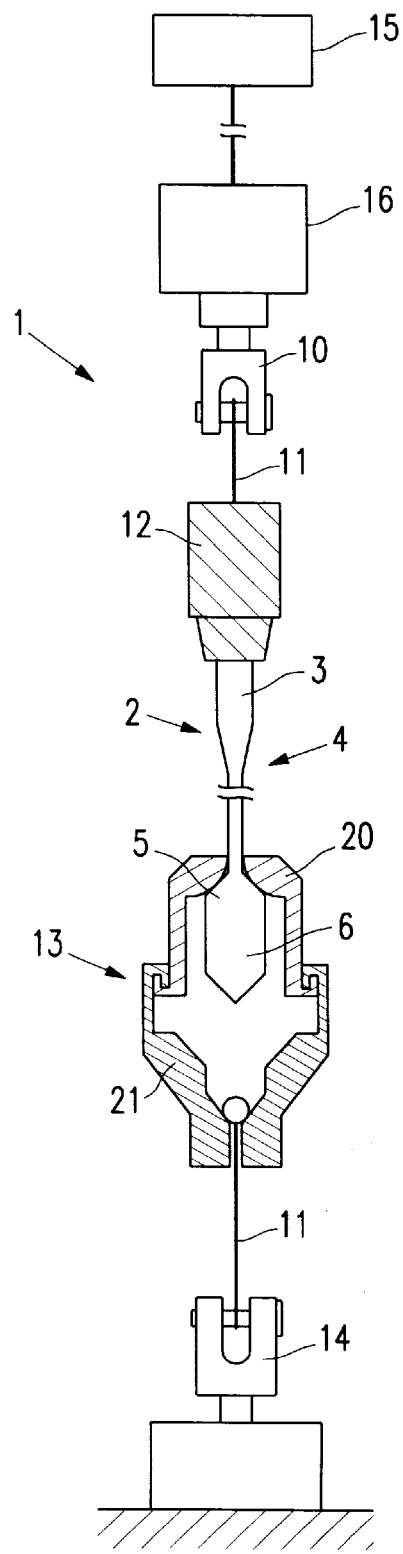
FIG. 1 shows a schematic explanatory view representing an example of an apparatus of the present invention for measuring mechanical strength of a neck portion of silicon single crystal.

FIG. 1 is a schematic explanatory view representing an exemplary apparatus for measuring mechanical strength of a neck portion of silicon seed crystal according to the present invention.

As shown in FIG. 1, the apparatus 1 for measuring mechanical strength of a neck portion has a structure where a seed chuck 12 for holding a seed crystal 3 of a test sample 2 is provided at an end of a wire 11 hung from an upper hook 10, and a crystal holder 13 for holding the other end part of the test sample from below is tied to a lower hook 14 with another wire 11 to support the holder, and comprises a tensile driving mechanism 15 for pulling the upper hook 10 at a predetermined rate, and a load transducer 16 for continuously measuring the tensile load. The hook to be pulled may of course be the lower hook 14, or the both of the hooks. As the tensile driving mechanism 15, a pulling mechanism, a motor and a pulley used for a crystal pulling apparatus according to CZ method can be used. A load cell, a spring balance, a weighing machine and the like can be used as the load transducer 16.

The seed chuck 12 may be one similar to that used in practically used pulling apparatuses. While it can hold the seed crystal 3 with a pin penetrated into a perforation of the seed crystal 3, a key inserted into a recess, a plurality of claws for grasping the seed crystal or the like, it is preferably one similar to that actually used for upwardly pulling heavy crystals for accurate measurement.

Figure 2A:
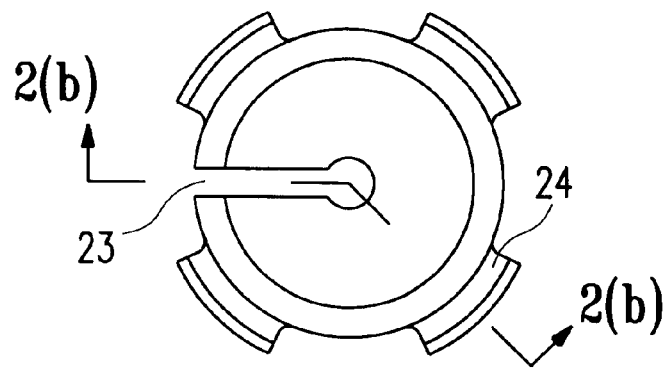
FIG. 2 shows a reversed bowl-like member of a crystal holder ((a); plan view, (b); sectional view)
Figure 2B:
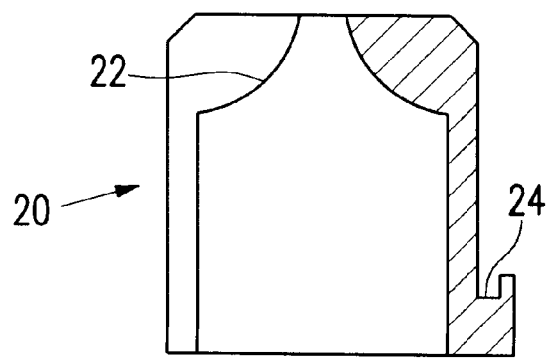

The crystal holder 13 comprises the reversed bowl-like member 20 and the bowl-like member 21 engaged with the reversed bowl-like member. As shown in FIG. 2, the reversed bowl-like member 20 is formed to have an internal tapered portion 22 approximately corresponding to the external configuration of the small diameter corn-shaped portion 5 for holding the conical section of the small diameter corn-shaped portion 5 following the seed crystal 3 and neck portion 4 of the test sample 2. When the test sample is set into the reversed bowl-like member, the neck portion can be inserted into it through a slit 23, and then the small diameter corn-shaped portion can be put into it. The reversed bowl-like member 20 has a flange 24 for engaging with the bowl-like member 21. The lower bowl-like member 21 is connected to the lower hook 14 with the wire 11, and serves as a support for the sample during the pulling, and as a receiving pan for the sample after breakage.

By fixing the small diameter corn-shaped portion and the rounded tail of the test sample with this crystal holder, the corn-shaped portion is fixed so that its center axis should be correctly along the vertical axis between the upper and lower hooks. Therefore, accurate tensile fracture strength can be obtained.

Figure 5:
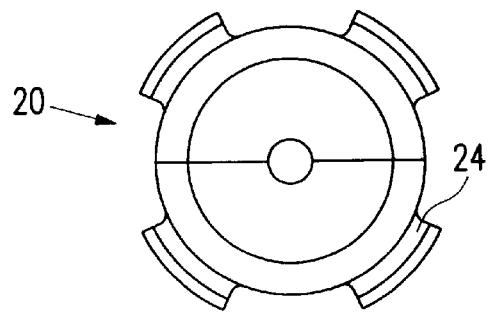
FIG. 5 is a plan view of another example of a reversed bowl-like member of a crystal holder.

As another example of the reversed bowl-like member 20, a two-piece type one can also be mentioned as shown in FIG. 5, which has a through hole for receiving the neck portion in the center thereof. The bowl-like member 21 for it may be the same one as mentioned above. They function in the same manner and exert the same advantages as described above.

In this way, by connecting the upper hook and the upper seed chuck, and the lower crystal holder and the lower hook with a wire respectively, the upper seed chuck and the lower crystal holder holding the test sample can be accurately positioned along the vertical axis between the upper hook and the lower hook. Thus, force is applied to the test sample only in the vertical direction, and hence a true value of tensile fracture strength of the neck portion of the seed crystal can be obtained. Further, if a safety factor calculated from tensile fracture strength obtained based on measurement by the aforementioned apparatus is used as a condition for the production of single crystal, it will sufficiently meet security against the future production of further larger diameter and weight of silicon single crystal.

The apparatus for measuring mechanical strength of a neck portion according to the present invention can further comprise a heating mechanism to permit measurement of mechanical strength of the neck portion under high temperature environment.

In such an apparatus, the test sample can be placed in the same temperature condition as an actually operating apparatus for pulling single crystals, and thus it becomes possible to measure more accurate and precise tensile fracture strength.

Figure 3:
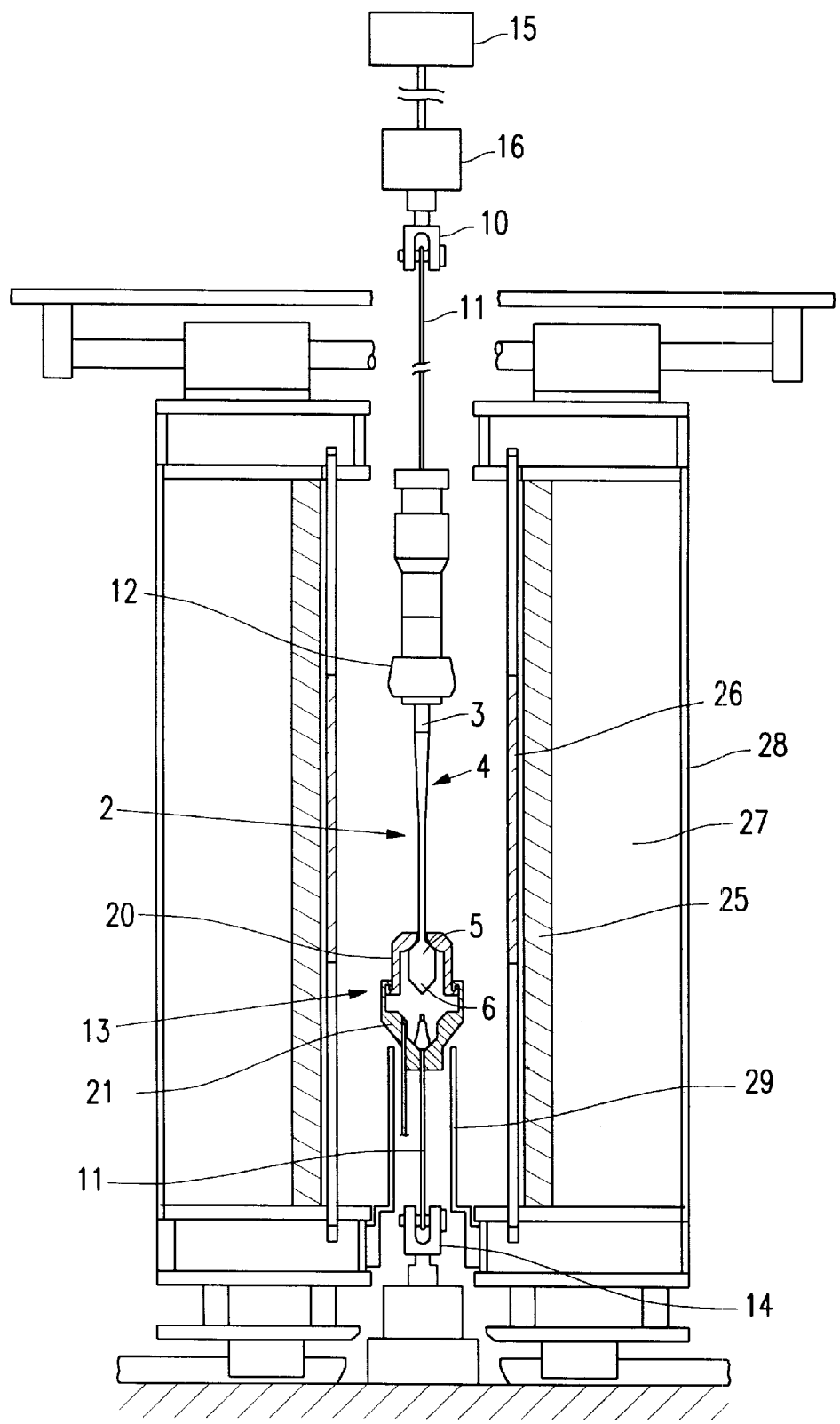
FIG. 3 shows a structure of an apparatus of the present invention for measuring mechanical strength of a neck portion, which is provided with a heating mechanism.

As an example of the apparatus provided with a heating mechanism, the apparatus can be constituted as shown in FIG. 3. In the apparatus shown in FIG. 3, the whole apparatus shown in FIG. 1 is placed in a cylindrical housing 28, and the neck portion can be heated by a heat source surrounding it. As the heat source, those utilizing radio-frequency heating, resistance heating or the like can be used. The sample temperature is measured from the reversed bowl-like member 20 by a thermocouple 29. In the example shown in FIG. 3, the measuring apparatus is accommodated in a graphite cylinder 25 provided in the housing 28, a heating wire 26 of resistance heating type is disposed in the proximity of the neck portion 4, and the graphite cylinder 25 is covered with a heat-insulating material 27.

The method for measurement by utilizing the apparatus for measuring mechanical strength of a neck portion of silicon seed crystal explained above will be described hereinafter.

A seed crystal 3 of test sample 2 which comprises seed crystal 3, neck portion 4, corn-shaped portion 5 and rounded tail 6, and was produced by an apparatus for pulling a silicon single crystal, is inserted into the seed chuck 12 provided at an end of the wire hung from the upper hook and held thereby, the portion of small diameter corn-shaped portion 5 and rounded tail 6 of the sample is fixed in the crystal holder 13 which is tied to a lower hook with a wire, and then the hook(s) is(are) pulled at a predetermined rate to measure tensile fracture strength.

In this case, the test sample is typically pulled by a tensile driving mechanism 15 provided above the sample, but it may be pulled by a tensile driving mechanism conversely provided under the sample.

In the above method, the seed crystal holding mechanism and the pulling mechanism using wires of the measuring apparatus for measuring mechanical strength of neck portion are substantially the same as those in a practical apparatus for pulling single crystals, and the test sample is one taken from actually operating apparatus for pulling single crystals, and comprises a seed crystal, neck portion, corn-shaped portion and rounded tail portion. Therefore, the test sample can be set between the seed chuck and she crystal holder without being applied with undue force, and as for the pulling operation, because the pulling can be surely performed along the perpendicular axis between the upper hook and the lower hook, a true value of tensile fracture strength can be obtained.

Figure 4:
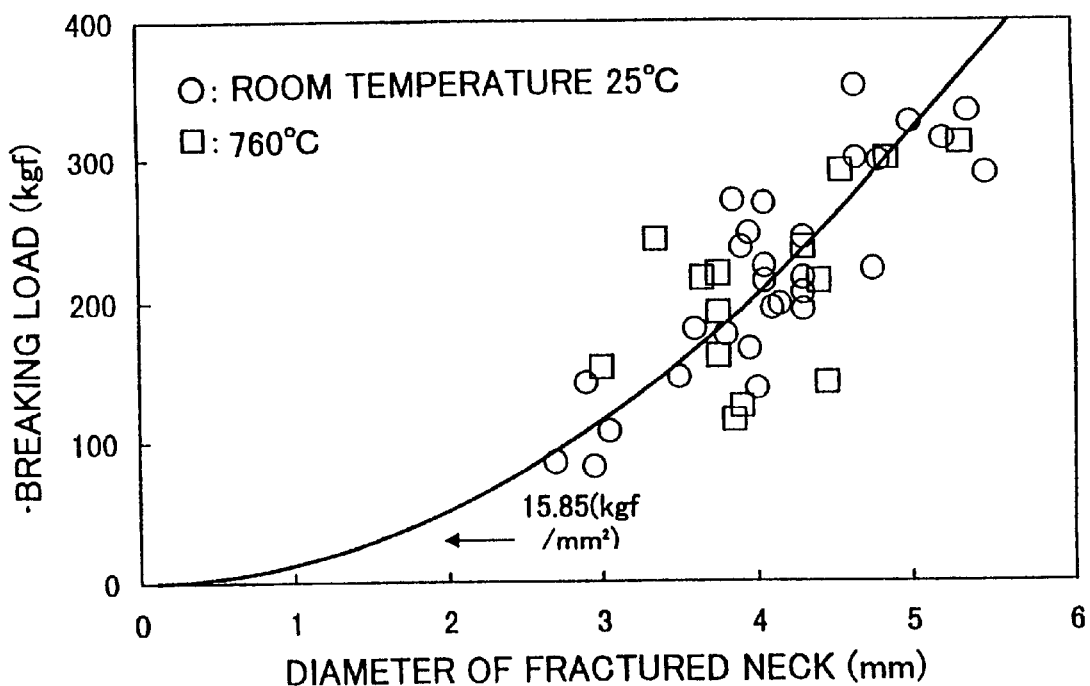
FIG. 4 is a graph representing relationship between fractured neck portion diameter and breaking load observed using a measuring apparatus of the present invention.

Exemplary results obtained by using the apparatus and the method for measuring mechanical strength of the neck portion of the present invention explained above are shown in FIG. 4. The test samples were subjected to the necking operation in a practically used pulling apparatus to have various diameters of the neck portion, and subsequently the corn-shaped portions and rounded tails were formed. The apparatus shown in FIG. 3 was used as the measuring apparatus, and tensile fracture strength was measured at ambient temperature and at a high temperature of 760° C. In FIG. 4, the breaking load is plotted to the diameter of the fractured neck portion, and the average breaking load per unit area obtained by the least squares method was 15.85 $kgf/mm^2$.

Accordingly, in the growing of silicon single crystal according to the Czochralski method, if the pulling operation is performed at a load applied to a neck portion of silicon seed crystal of 15.85 $kgf/mm^2$ or less, possibility of breakage at least at the seed crystal or the neck portion is lowered, and if performed at 0.9×15.85 $kgf/mm^2$ considering a safety factor, the possibility is eliminated.

In other words, for example, when the minimum diameter of the neck portion is 4 mm, a single crystal weight of $(4)^2 \cdot \pi/4 \cdot 15.85 = 199$ kg or less can safely be pulled upwardly.

Thus, a safety factor calculated from tensile fracture strength obtained based on measurement by the aforementioned apparatus of the present invention can be used as a condition for the production of single crystal, to sufficiently meet security against future production of larger diameter and weight of silicon single crystal, and improve productivity and production yield.

Further, the pulling operation is preferably performed so that the load applied to the neck portion of silicon seed crystal should be $0.6 \times 15.85$ kgf/mm$^2$ or more.

By providing a lower limit as defined above, productivity above a certain level can be ensured. Formerly, because the mechanical strength of the wire was indefinite and hence the upwardly pulling weight was unduly reduced, and excessively high safety factor was used, thereby the productivity and the yield were deteriorated. In contrast, according to the present invention, a predetermined productivity can be ensured by performing the pulling operation at a load of 60% or more of the critical value. Such a load also prolongs the lifetime of the wires.

Further, with the tendency to larger diameter of crystals, the weights of the corn-shaped portion and the rounded tail of the single crystal become larger, and their ratio to the crystal weight tends to become larger. For example, the total weight of the corn-shaped portion and the rounded tail of a single crystal having a diameter of 200 mm is about 10 kg, whereas the total weight of the corn-shaped portion and the rounded tail of a single crystal having a diameter of 300 mm becomes about 35 kg. In case of the CZ method, the weight increase of the corn-shaped portion is not so large, but the weight increase of the rounded tail is serious.

For exemplification, ratios of the total weight of the corn-shaped portion and the rounded tail relative to the crystal weight for the case where a crystal having a diameter of 300 mm is pulled with a neck portion diameter of 4.5 mm are shown in Table 1. The total weight of the corn-shaped portion and the rounded tail is determined as 35 kg.

TABLE 1

| Ratio to Critical value | Crystal weight (kg) | Weight ratio (%) |
|---|---|---|
| 1.0 | 252 | 13.9 |
| 0.9 | 227 | 15.4 |
| 0.8 | 202 | 17.3 |
| 0.7 | 176 | 19.9 |
| 0.6 | 151 | 23.2 |
| 0.5 | 126 | 27.8 |

As seen from Table 1, the weight ratio of the corn-shaped portion and the rounded tail to the whole crystal is 23.2% when the pulling operation is performed at $0.6 \times 15.85$ kgf/mM$^2$, whereas when the pulling operation is performed at $0.5 \times 15.85$ kgf/mm$^2$, it is 27.8%, which exceeds ¼ of the crystal weight. Therefore, as for crystals of a large diameter, the yield improvement can be obtained in a sufficient extent by performing the pulling operation at a load of 60% or more of the critical value.

The present invention is not limited to the embodiment described above. The above-described embodiment is a mere example, and those having the substantially same structure as that described in the appended claims and providing the similar functions and advantages are included in the scope of the present invention.

For example, because true mechanical strength of a silicon single crystal can be measured according to the present invention, a value not more than the strength can principally be of course applied to pulling operation of any single crystal ingots having any diameter, length and/or weight. That is, it is useful for the pulling operation of crystals having a diameter of 200 mm or 300–400 mm recently used, because the mechanical strength becomes particularly important in such a case.

The present invention can of course be applied not only to the ordinary Czochralski method but also to the MCZ method (Magnetic Field Applied Czochralski Crystal Growth Method) in which a magnetic field is applied when a silicon single crystal is pulled.

What is claimed is:

1. A method for measuring mechanical strength of a neck portion of silicon seed crystal used for growing a silicon single crystal by the Czochralski method, wherein a seed crystal of a test sample which comprises seed crystal/neck portion/small diameter corn-shaped portion/rounded tail and is produced by an apparatus for pulling a silicon single crystal, is inserted into a seed chuck provided at an end of a wire hung from an upper hook and held thereby, the small diameter corn-shaped portion/rounded tail of the sample is fixed in a crystal holder which is tied to a lower hook with another wire, and then the hook(s) is(are) pulled at a rate to measure tensile fracture strength.

2. A method for producing a silicon single crystal, wherein pulling operation in growing a silicon single crystal by the Czochralski method is performed so that load applied to a neck portion of silicon seed crystal should be 15.85 kgf/mm$^2$ or less.

3. The method for producing a silicon single crystal according to claim 2, wherein the pulling operation is performed so that the load applied to the neck portion of the silicon single crystal should be $0.9 \times 15.85$ kgf/mm$^2$ or less.

4. The method for producing a silicon single crystal according to claim 3, wherein the pulling operation is performed so that the load applied to the neck portion of the silicon single crystal should be $0.6 \times 15.85$ kgf/mm$^2$ or more.

5. The method for producing a silicon single crystal according to claim 2, wherein the pulling operation is performed so that the load applied to the neck portion of the silicon single crystal should be $0.6 \times 15.85$ kgf/mm$^2$ or more.

* * * * *